United States Patent [19]

Maggio

[11] Patent Number: 4,859,610
[45] Date of Patent: Aug. 22, 1989

[54] IMMUNOASSAY INCUBATION DEVICE

[75] Inventor: Edward T. Maggio, San Diego, Calif.

[73] Assignee: Synbiotics Corporation, San Diego, Calif.

[21] Appl. No.: 906,663

[22] Filed: Sep. 12, 1986

Related U.S. Application Data

[63] Continuation-in-part of Ser. No. 741,369, Jun. 5, 1985, abandoned.

[51] Int. Cl.$^4$ ............................................. G01N 33/483
[52] U.S. Cl. ..................................... 436/518; 422/58; 422/61; 422/101; 422/102; 435/7; 435/296; 435/311; 435/312; 435/809; 436/531; 436/66; 436/177; 436/178; 436/808; 436/810
[58] Field of Search ....................... 422/57, 58, 61, 102, 422/101; 436/66, 177, 178, 531, 807, 808, 810, 518; 435/7, 296, 311, 312, 809

[56] References Cited

U.S. PATENT DOCUMENTS

| | | | |
|---|---|---|---|
| 3,083,145 | 3/1963 | Ryan | 435/296 |
| 3,819,045 | 5/1972 | Greenwald | 436/178 |
| 3,844,895 | 10/1974 | Rose et al. | 435/296 X |
| 3,936,373 | 2/1976 | Studer | 422/255 X |
| 4,007,012 | 2/1977 | Greenwald | 422/102 X |
| 4,022,576 | 5/1977 | Parker | 436/177 |
| 4,066,646 | 1/1978 | LeBlanc, Jr. et al. | 422/102 |
| 4,070,249 | 1/1978 | Janin et al. | 422/102 X |
| 4,092,120 | 5/1978 | Suovaniemi et al. | 422/58 X |
| 4,135,884 | 1/1979 | Shen | 422/58 X |
| 4,225,575 | 9/1980 | Piasio et al. | 436/810 X |
| 4,288,316 | 9/1981 | Hennessy | 422/101 |
| 4,305,924 | 12/1981 | Piasio | 436/810 X |
| 4,427,769 | 1/1984 | Adlercreutz et al. | 422/61 X |
| 4,482,521 | 11/1984 | Bunce et al. | 422/69 X |
| 4,580,577 | 4/1986 | O'Brien et al. | 422/101 X |
| 4,599,219 | 7/1986 | Cooper et al. | 422/58 X |
| 4,635,488 | 1/1987 | Kremer | 422/58 X |
| 4,678,559 | 7/1987 | Szabados | 422/101 X |

OTHER PUBLICATIONS

Sale literature from "Euszo Pharmaceuticals", 2 sheets.

Primary Examiner—Michael S. Marcus
Assistant Examiner—Jill Johnston
Attorney, Agent, or Firm—Martin A. Voet

[57] ABSTRACT

An immunoassay incubation device is employed for detecting the presence of specific analytes in solid and semisolid compositions using solid phase immunoassay methods. Analysis of such compositions by solid phase immunoassay first requires that soluble or particulate analytes be extracted from the sample composition. A representative example of such composition is fecal material. The immunoassay incubation device includes a vessel for homogenizing the sample composition. The device also includes a solid phase assay member immunologically sensitized for detecting particular analytes. After the sample composition is homogenized, the assay member is incubated in an incubation chamber which is immersed into the homogenate within the homogenization vessel. The incubation chamber includes a screen which screens out unextracted components from the homogenate while passing extracted components. The invention discloses that contact with unextracted components from such compositions can degrade the accuracy of solid phase immunoassays.

25 Claims, 4 Drawing Sheets

IMMUNOASSAY INCUBATION DEVICE

This is a continuation-in-part of application Ser. No. 741,369, filed 6/5/85, now abandoned.

BACKGROUND OF THE INVENTION

The invention relates to devices and methods for homogenizing solid or semi-solid compositions and for performing solid phase immunoassays on the resultant homogenate. The invention is particularly useful for homogenizing fecal samples and detecting specific analytes therein.

The invention is employed for the analysis of a class of solid and semisolid compositions which include a mixture of extractable and unextractable components. The extractable components of such compositions may include one or more soluble or particulate analytes which, when isolated, can be analyzed using prior art solid phase immunoassay technology. Within the class of solid and semisolid compositions are included fecal materials; sludges; a variety of cellular materials, e.g. ground meat and vegetable matter, biopsy and necropsy samples, sputum, and cell scrapings from various tissues; and a variety of other biological and environmental materials. A number of compositions within this class are difficult to handle because they are noxious and/or hazardous. Each of these solid and semisolid compositions may potentially contain one or more extractable analytes having clinical or commercial significance. Examples of extractable analytes include many infectious organisms, toxins, pesticide or other chemical residues, drugs, cancer markers, nutritional components, and many others.

A prior art solid phase immunoassay for detecting occult hemoglobin in fecal material is described in U.S. Pat. No. 4,427,769 (Adlercreutz). Adlercreutz describes a two step process for detecting occult hemoglobin: 1. One side of a filter paper is contacted with a sample of fecal material for absorbing occult hemoglobin and passing occult hemoglobin to an absorbant which contacts the opposite side of the filter paper; and 2. After having absorbed occult hemoglobin, the adsorbant is then transferred to an assay vessel for desorbing the hemoglobin and performing the solid phase immunoassay. Adlercruetz's process discloses a method for maintaining a separation between unhomogenized fecal material and solid phase immunological reagents. Because the fecal material of Adlercreutz's process is unhomogenized, much of the occult hemoglobin will often remain sequestered and inaccessible for analysis within the sample material. Adlercreutz's process is best employed with samples of fecal material having abundant occult hemoglobin uniformly distributed within the sample.

If a solid or semisolid sample is unhomogenized and if analyte is distributed inhomogeniously within the sample, the relative inaccessibility of analyte within the sample may render a measurement of analyte unrepresentative of the whole sample. What is needed is a device which can homogenize or disperse compositions within this class and which can analyze the resultant homogenate employing solid phase immunoassay technology. In those cases where the sample is noxious or hazardous, it would also be preferred that the sample remain isolated within the device during the assay process.

SUMMARY OF THE INVENTION

The present invention discloses an immunoassay incubation device and method for homogenizing solid or semisolid compositions and analyzing the resultant homogenate using solid phase immunoassay techniques. The immunoassay incubation device includes a homogenization vessel for homogenizing the sample and an insert positioned within the vessel for providing an incubation chamber for solid phase immunological reagents. An essential feature of the immunoassay incubation device is a screen incorporated into the insert which passes extracted components, including analyte, from the homogenate into the incubation chamber while screening out unextracted components. The present invention discloses that homogenization alone can either enhance or diminish the sensitivity and accuracy of a solid phase immunoassay, depending upon the characteristics of the particular sample being analyzed. On the one hand, homogenization may enhance the sensitivity of an assay by increasing the accessibility and uniformity of extracted components, including analyte. On the other hand, homogenization can also diminish the accuracy of the assay by increasing the presence and accessibility of unextracted components. The invention discloses that a screen can be employed with homogenates to maintain the enhanced sensitivity of an assay caused by the increased accessibility of analyte and, at the same time, recapture the accuracy of the assay which was diminished by the presence of unextracted components.

There are several mechanisms whereby the accuracy of an immunoassay can be diminished by the increased presence of unextracted components. Unless unextracted components are screened from the incubation chamber, the increased presence of unextracted components will increase the contact and nonspecific binding between the unextracted components and the solid phase immunological reagents and the underlying support for such solid phase immunological reagents. Such increased contact and binding may physically block analyte from binding to the same solid phase immunological reagents during the incubation step. If unextracted components remain bound to the solid phase immunological reagents after the incubation step, the continued presence of such unextracted components may block the binding of subsequently added antibody reagents, i.e. reagents for labeling bound analyte. Alternatively, subsequently added antibody reagents may bind nonspecifically to unremoved unextracted components. Depending upon which mechanism predominates, the continued presence of unremoved unextracted components after the incubation step may lead to either diminished sensitivity or to false positive results. Unextracted components nonspecifically bound to solid phase immunological reagents may be difficult to remove after the incubation step. The present invention discloses a device for enhancing and recapturing the accuracy of solid phase immunoassays. The present invention discloses an immunoassay incubation device having a screen for passing analyte from a homogenate into the incubation chamber while excluding the passage of unextracted components from such chamber.

In a preferred embodiment, the immunoassay incubation device encloses the sample and isolates the sample from the user during processing. This preferred embodiment is particularly useful for analyzing hazardous or noxious materials, e.g. fecal and diarrheal materials, sputum, sludge, vomitus, pus, biopsy and necropsy samples. This preferred embodiment isolates the user from exposure to noxious fumes, infectious agents, chemical poisons, and the like arising from the sample during homogenization and incubation. Additionally, the device minimizes the handling and transfer of the sample material so as to minimize the opportunity for contamination of the user through spillage, aerosol generation and splashing.

The present invention discloses a device and a method which employs homogenization for enhancing the sensitivity and reliability of solid phase immunoassay techniques for analyzing solid and semisolid materials. The present invention discloses the employment of a screen for maintaining a separation between unexpected components and solid phase immunological reagents. The present invention discloses a device and method for integrating the steps of homogenization, separation, and assay incubation. The present invention discloses a device for enclosing noxious and hazardous materials while performing these functions. The present invention discloses an efficient method for measuring sample material for homogenization. The present invention discloses a convenient transport vessel for unprocessed or partially processed samples so that samples may be collected, transported and tested at a later time. The present invention discloses an efficient method for prepackaging immunological reagents and nonimmunological test reagents into the incubation chamber.

DETAILED DESCRIPTION

Figure 3:
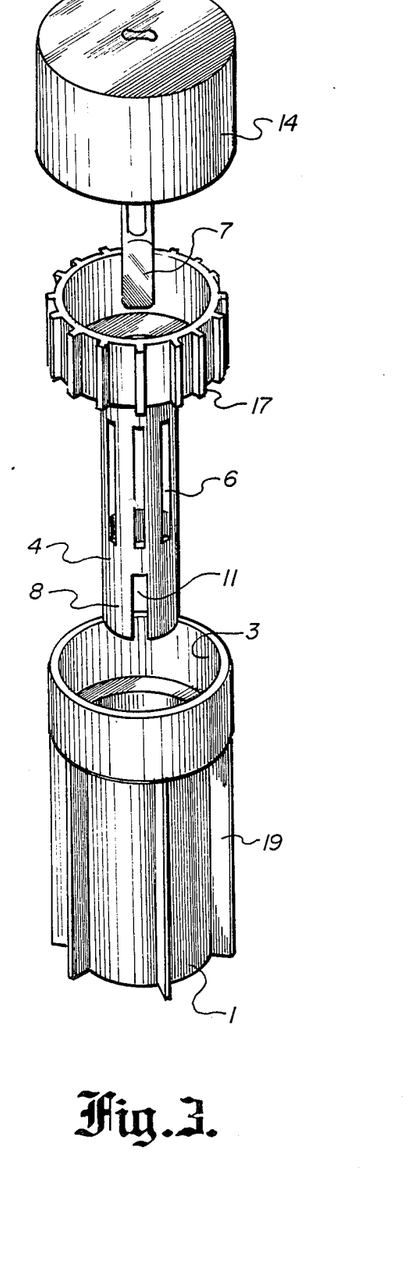
FIG. 3 is an exploded view in perspective of the immunoassay incubation device of FIG. 1.

An exploded view of a preferred embodiment of the immunoassay incubation device is illustrated in FIG. 3. This preferred embodiment of the device is particularly useful for homogenizing and analyzing fecal samples. This preferred embodiment includes a vessel (1) having an interior portion (2) for housing structural components and containing homogenization fluids. An opening (3) in the vessel (1) allows materials to be introduced and removed from the interior portion (2). An insert (4) is designed to fit within the interior portion of the vessel (1). The insert (4) is hollow and defines an incubation chamber (5). During an incubation procedure, the insert (4) is positioned within the vessel (1) so that the incubation chamber (5) is partially emersed within the homogenate.

The insert (4) includes a screen (6). The screen (6) is composed of a plurality of openings in the insert (4). The function of the screen (6) is to allow fluid to pass between the interior portion of the vessel (2) and the incubation chamber (5), but to exclude the passage of unextracted sample components from entry into the incubation chamber (5). A preferred embodiment of the screen (6) is illustrated in FIG. 3. The screen (6) is illustrated here as a plurality of vertical slots. These vertical slots or apertures may be positively immersible with respect to the liquid medium. To be positively immersible means that both sides of the apertures are positively immersible with respect to the liquid medium which adjacent faces these apertures, i.e. the apertures lie below the topmost part of the liquid medium which adjacently faces these apertures. The preferred width for these slots is exaggerated in FIG. 3 for illustration purposes. The actual preferred width for screening unextracted components from homogenized human fecal material is approximately 1 mm. However, the holes of the screen (6) may have any geometry which effectively excludes unextracted components while allowing extracted components to pass freely.

In other words, the ability of the screen to exclude unextracted components is determined by the cross sectional diameter of the holes or apertures; while the ability of extracted components or soluble analytes to freely pass across the screen is determined by the cross sectional area of the holes or apertures. Holes or apertures with a relatively small cross sectional diameter are desirable because they exclude even small diameter unextracted components; while apertures with a large cross sectional area are desirable because they allow soluble analytes to pass more freely across the screen. FIG. 3 illustrates a device having a screen (6) which has both a relatively small cross sectional diameter and a relatively large cross sectional area.

When the immunoassay incubation device is operated, one or more assay members (7) may be introduced into the incubation chamber (5). These assay members (7) are devices which have immunological reagents or other binding reagents anchored on underlying solid phase support. The example section below discloses several immunoassay members (7) having immunological reagents coated onto a solid phase. Examples of antibody used for coating the assay members include anti-E. histolytica, anti-chlamydia, anti-HSV, and anti-human hemoglobin. The antibody may be either monoclonal or polyclonal. Methods for anchoring antibody to a solid phase support are provided in the example section. The performance of these solid phase immunological reagents can be impaired by direct contact with solid or semisolid sample material and by contact with unextracted components within an homogenate of such solid or semisolid sample material. It is the essential function of the screen (6) to shield assay members (7) incubating within the incubation chamber (5) from contact with unextracted sample components.

Figure 1:
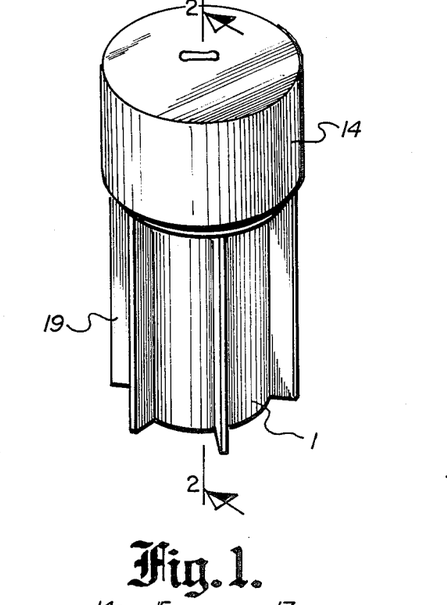
FIG. 1 is a perspective view of a preferred embodiment of the immunoassay incubation device.
Figure 2:
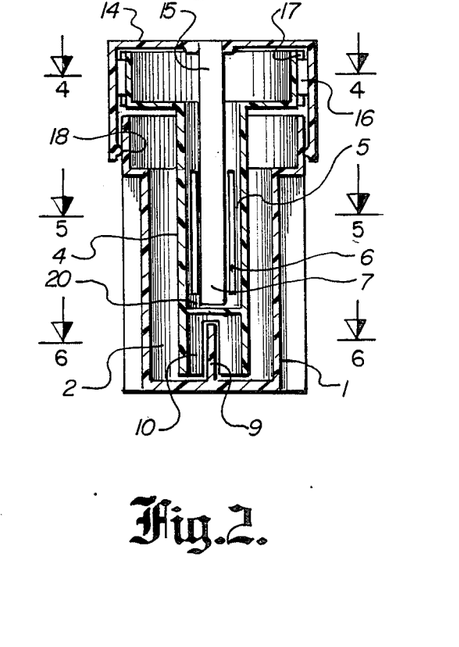
FIG. 2 is a sectional view of the immunoassay incubation device of FIG. 1, illustrating the configuration of the dip stick within the insert.
Figures 4, 5, 6, 7, 8:
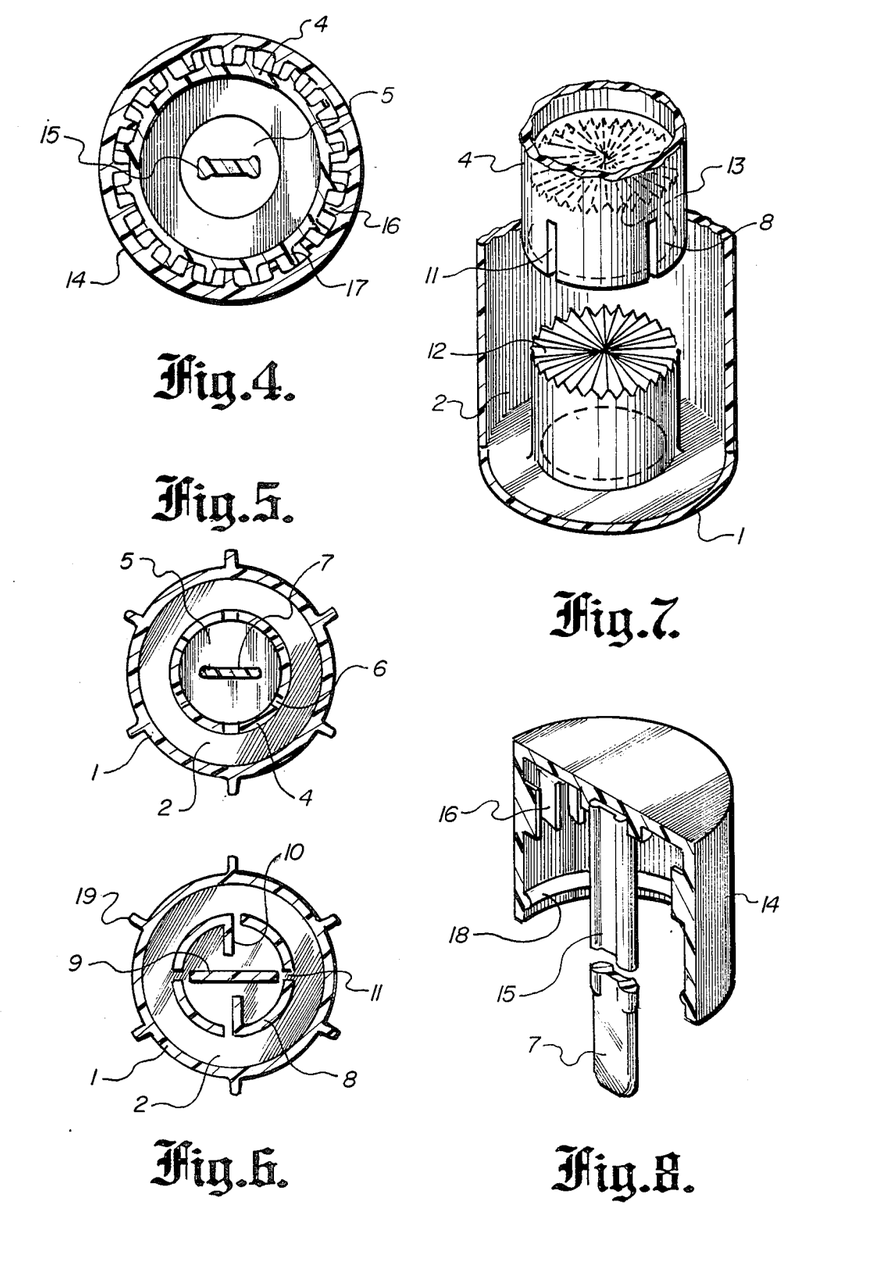
FIG. 4 is a sectional view of the immunoassay incubation device of FIG. 2, illustrating the cap, the insert, and the teeth for engaging the insert with the cap.
FIG. 5 is a sectional view of the immunoassay incubation device of FIG. 2, illustrating the vessel, the incubation chamber, and the bottom portion of the dip stick which provides the underlying support for the solid phase immunological reagents.
FIG. 6 is a sectional view of the immunoassay incubation device of FIG. 2, illustrating the vessel, the scoop for securing and transferring sample material, and the vanes for homogenizing the sample.
FIG. 7 is partially a sectional view and partially a perspective view of an alternative embodiment of the immunoassay incubation device, illustrating grinding members for homogenizing the sample.
FIG. 8 is partially a sectional view and partially a perspective view of the immunoassay incubation device of FIG. 2, illustrating the cap, the dip stick, and the teeth for engaging the cap to the insert.

FIG'S. 2 and 6 illustrate a scoop (8) extending from the bottom of the insert (4) for securing a reproducible volume or reasonably reproducible volume of the sample material. A reproducible volume of sample material is secured by pressing the scoop (8) into the sample material removing a plug. Once a plug of sample material is secured in the scoop (8), the plug is then transferred to the vessel (1) together with the insert (4). When the insert (4) is introduced into the vessel (1), it is axially centered with the vessel (1) by inserting the stationary vane (9) into the scoop (8) and interlocking the stationary vane (9) with the rotatable vanes (10). The stationary vane is fixed to the bottom of the interior of the vessel (1). The rotatable vanes (10) are nested within the scoop (8) and are fixed to the insert (4), which is rotatable within the vessel (1).

This arrangement of rotatable and stationary vanes is one possible embodiment of the means for extracting the sample analyte.

Homogenization of the sample plug is achieved by pipetting a buffer solution into the vessel (1) and rotating the insert (4) approximately 90 to 120 degrees in alternating directions with a back and forth motion for about twenty cycles. The interlocking vanes (9 & 10) disperse and homogenize the plug. The homogenized material escapes from the scoop (8) during the homogenization process through slots (11). The homogenization process extracts soluble and particulate matter from the sample. However, if the sample includes unextractable components or difficult to extract components, these components may also escape through the slots (11) and enter the homogenate. It is an essential feature of this invention that these unextracted components are excluded from the incubation chamber (5).

FIG. 7 illustrates an alternative embodiment of the homogenization means. This embodiment has special application for homogenizing tissue samples and other materials that are difficult to disperse. A fixed grinding member (12) is attached to the bottom of the vessel (1) and a rotatable grinding member (13) is nested within the scoop (8) and attached to the insert (4). When the scoop (8) is introduced into the vessel (1) with a plug of tissue sample, rotation of the insert (4) with respect to the vessel (1) while exerting downward pressure will extract soluble and particulate components from the plug and will cause these components to escape through the slots (11) and be dispersed into the homogenization fluid. FIG. 7 illustrates congruent grinding surfaces for homogenizing sample material. However, fixed and rotatable serrated surfaces juxtaposed to one another may also be employed for homogenizing sample materials which are difficult to disperse.

These arrangements of congruent fixed and rotatable grinding members or fixed and rotatable serrated surfaces are possible embodiments of the means for extracting the sample analyte.

In an alternative embodiment not shown in the drawings, the vessel (1) and the insert (4) are adapted for extracting material from swabs. A detailed description of this embodiment is provided in Examples 4 and 5.

If the immunoassay device is to be employed for processing noxious or hazardous sample materials, the device may include a cap (14). The cap (14) fits over the insert (4) and covers the opening (3) of the vessel (1). The cap (14) may include a dip stick (15). The dip stick (15) is a shaft structure which attached to the cap (14) and extends downward into the incubation chamber (5). The dip stick (15) is employed for introducing the assay member (7) into the incubation chamber (5). In the preferred mode, when the cap (4) is replaced on the vessel (1), the dip stick (15) will extend into the incubation chamber (5) with the assay member (7) positioned in the bottom half of the incubation chamber. The assay member (7) includes an immunologically sensitized solid phase structure or other binding reagents for detecting analytes extracted from the sample. The underlying solid phase support of the assay member (7) may be constructed from the bottom portion of the shaft of the dip stick (15) or may be constructed from other structures, e.g. balls, beads or other structures. In alternative embodiments of the invention, the assay member (7) need not be attached to a dip stick (15). When noxious or hazardous materials are analyzed, the cap (14) serves to enclose the contents of the vessel (1) and also serves as a convenient handle for the dip stick (15).

In a preferred embodiment, the cap (14) may be engaged with the insert (4) for transmitting rotational motion. When complimentary gear teeth (16 & 17) on the cap (14) and the insert (4) are intermeshed, the cap (14) becomes engaged with the insert (4). Rotating the cap (14) will then cause the insert (4) to rotate. This preferred embodiment may also include a seal (18) for sealing the cap (14) to the vessel (1) so as to enclose noxious or hazardous materials within the vessel (1) during the homogenization and incubation processes. Support structures (19) on the outside of the vessel (1) help the user to maintain a grip on the vessel (1) with one hand while rotating the cap (14) with the other hand.

An alternative embodiment of the invention includes a well (20) in the bottom of the incubation chamber (5). In a preferred embodiment, the well (20) extends below the screen (6) about 3 mm. Immunoassay incubation devices with such wells (20) may be manufactured with a deposit of dried reagents therein. Protocols for depositing a number of dried agents are disclosed in the Example section (infra). Typically, these dried reagents will include antibody enzyme conjugates for labeling analyte which binds to the assay member (7). Preferred enzyme labels include horseradish peroxidase, glucose oxidase, and alkaline phosphatase.

Another alternative embodiment of the invention includes valve means for controlling the passage of sample fluid from the vessel (1) into the incubation chamber (5). For certain samples, it is advantageous to wait until the homogenization process is completed before allowing the sample fluid to pass into the incubation chamber (5). The valve means may include a depression (21) in the wall of the vessel (1) and a small hole (22) passing through the wall of the incubation chamber (5). In the preferred version of this alternative embodiment, the small hole (22) passes through a protuberance (23) arising radially from the wall of the incubation chamber (5). When it is desired to pass homogenized sample fluid from the vessel (1) into the incubation chamber (5), the insert (4) is rotated until the depression (21) and the hole (22) become aligned. The insert (4) may include multiple protuberances (23) symmetrically arrayed around the exterior wall of the incubation chamber (5) for maintaining a constant space between the insert (4) and the vessel (1). However, not all protuberances (23) necessarily have a corresponding hole (22).

The insert (3) of this alternative embodiment may include two or more normal stops (24) and a final stop (25). When the insert (3) is fully inserted into the vessel (1), the normal stops (24) define the limits of the rotational movement of the insert (3) within the vessel (1) for homogenizing the sample. As the insert (3) is twisted within the vessel (1), a normal stop (24) will come into contact with a stationary vane (9), thereby preventing further rotation. If the insert (3) is slightly raised within the vessel (1), the insert may then be further rotated, passing by the normal stop (24), until the stationary vane (9) contacts the final stop (25). When the final stop (25) abuts the stationary vane (9), the depression (21) will align with the hole (22), thereby allowing fluid to pass from the vessel (1) into the incubation chamber (4).

This alternative embodiment may also include separate incubation chambers (26 & 27) separated by a partition (28). The first incubation chamber (26) is employed for exposing the dip stick (15) to the homogenized sample fluid. The second and subsequent incubation chambers (27) are employed for developing the color reaction on the dip stick (15) after it has been exposed. The valve means opens only into the first incubation chamber (26). Since the subsequent incubation chambers (27) are filled with development reagents, sample fluid is specifically excluded from these chambers (27). A sealing means, such as Mylar foil (29), may be employed to prevent contamination of the subsequent incubation chambers with sample fluid. In this embodiment, the dip stick (15) is positioned eccentrically with respect to the cap (14) so that the solid phase assay member (7) can be positioned within each one of the incubation chambers in turn. Protocols for the use of this embodiment of the invention are disclosed below in the Examples section, with particular reference to the use of the device for the detection of human hemoglobin.

Examples of the application of this invention are provided below. These examples are meant to be illustrative only and are not meant to limit the invention to the examples provided.

EXAMPLE 1

An immunoassay incubation device for detecting the presence of Entamoeba histolytica (E. histolytica) antigen in human stool samples may be constructed generally as illustrated in FIG. 2. The device includes a vessel (1) having fixed one or more homogenization vanes (9) attached to the bottom of the vessel (1). The bottom portion of the insert (4) has a scoop (8) and one or more rotatable homogenization vanes (10) nested within the scoop (8). The scoop (8) allows for precise or reasonably precise measurement of sample when the insert (4) is pressed into a stool sample. After sample material is secured in the scoop (8), the insert (4) may be introduced into the vessel (1). The fixed and rotatable homogenization vanes (9 & 10) become interlocked with one another when the insert (4) is introduced into the vessel (1). The device also includes a tightly fitting cap (14) which covers the insert (4) and seals the opening (2) of the vessel (1). The cap (14) and the insert (4) are engageable by interlocking teeth (16 & 17). When the cap (14) and the insert (4) are engaged, the cap (14) may be employed for rotating the insert (4) and homogenizing the sample. A dip stick (15) protrudes from the under side of the cap (14) and descends into the incubation chamber (5) of the insert (4) so as to approach the bottom of the incubation chamber (20).

Immunological dip sticks (15) with immunologically sensitized assay members (7) may be constructed by coating flattened polystyrene shafts with monoclonal anti-E. histolytica antibody (Synbiotics Catalog No. 15001). Polystyrene shafts, having approximate dimensions of 1 mm×5 mm×3 cm, are placed, one each, into 10×75 mm disposable test tubes to a depth of 0.5 cm in a solution of monoclonal anti-E. histolytica antibody (2–4 micrograms/ml) in pH 9.2 sodium borate buffer. Passive absorption of antibody onto the surface of the polystyrene shaft occurs when the bottom 0.5 cm portion of each shaft is allowed to contact the antibody solution for a period of three or four hours at room temperature. After this absorption process, the shafts are removed for the first set of 10×75 mm test tubes and placed, one each, into a second set of 10×75 mm test tubes to a depth of 1.0 cm in a solution of 1% bovine serum albumin (BSA), pH 7.4 PBS. After three hours, the shafts are removed from the BSA solution, washed in 0.05% Tween-20, PBS, and allowed to dry at ambient temperatures for 4 hours. Treatment with BSA reduces nonspecific binding to the antibody coated portion of the shaft during subsequent immunoassays. The sensitized dip sticks (15) may then be attached to caps (14). The bottom 0.5 cm portion of each dip stick (15), i.e. the portion coated with antibody, comprises the immunoassay member (7). The length of the dip stick (15) is chosen so that the immunoassay member (7) lies within the bottom half of the incubation chamber (5) when the dip stick (15) is inserted into the incubation chamber (5) and the cap (14) is sealed to the vessel (1) and engaged to the insert (4).

After a measured portion of sample material is secured by the scoop (8) and introduced into the vessel (1), 2 mils of phosphate buffered saline, pH 7.4 (PBS) is added to the vessel (1). The 2 mls of PBS submerges the stool sample within the scoop (8) and flows both inside and outside the incubation chamber (5). The vessel (1) is then sealed with the cap (14) and the cap (14) is engaged with the insert (4). The sample is then homogenized by rotating the insert (4) with a back and forth motion approximately 90–120 degrees in either direction. Homogenization of the stool sample in the PBS is complete after approximately 15 rotational cycles. If the device were uncapped, extracted stool sample could be seen to fill the incubation chamber (5) during the homogenization process. A screen composed of slots (6) in the side of the insert (4) allows extracted antigen from the homogenized sample to pass from the vessel (1) into the incubation chamber (5) while excluding unextracted components. The slots (6) prevent contact between unextracted components of the sample material and the immunological dip stick (15) in the incubation chamber (5). The slots (6) should be sufficient in number and should have sufficient lengths and widths so as to allow easy transfer of liquid between the interior portion of the vessel (2) and the incubation chamber (5). A preferred immunoassay incubation device for analyzing human fecal samples has four vertical slots running the length of the incubation chamber 95) and having widths of approximately 1 mm. The screening capacity of this preferred device is known to be sufficient to screen the entry of unextracted human fecal components into the incubation chamber (5). However, immunoassay incubation devices having screens (6) with other shapes, sizes, and pluralities may also be employed, particularly for analyzing sample sources other then human fecal material.

After homogenizing the sample material, the immunoassay member (7) is allowed to incubate for 15 minutes in the incubation chamber (5) with the extracted components of the fecal sample. During this incubation, analyte from the extracted fecal sample binds specifically to the assay member (7) portion of the dip stick. The cap (14) and dip stick (15) are then removed and withdrawn and the dip stick (15) is washed under cold tap water to remove unbound components. In a second incubation, bound analyte on the washed dip stick is then labeled using an enzyme conjugate. Horseradish peroxidase (HRP) covalently coupled to monoclonal anti-E. histolytica antibody may be employed as the enzyme conjugate. Anti-E. histolytica-HRP may be prepared according to the method of Nakane, et al. (Nakane, P. K., and Kawaio, A. T., Histochem and Cytochem, Vol. 22, 1084 (1974)).

After incubating the dip stick with enzyme conjugate for approximately 15 minutes, the dip stick is washed again under cold tap water to remove unbound enzyme conjugate. The enzyme conjugate which labels the analyte bound on the dip stick is then color developed. The dip stick is inserted into a substrate solution, e.g. phosphate buffered saline (PBS) containing 0.5 mg per milliliters of 4-chloronaphthol and 1.5 mM hydrogen peroxide, or 1.5 mM urea peroxide. Blue color deposited on the dip stick indicates the presence of E. histolytica antigen within the fecal sample.

The user may wish to compare the color reaction from test fecal material with the color reactions of control fecal material which is free of E. histolytica antigen and to which E. histolytica antigen has been added. In the later case, 500 trophs of E. histolytica antigen (ICN Medical Laboratories, Inc.; Portland, Oregon) may be added to 1 milliliter of fecal material. When control fecal material without E. histolytica antigen is tested according to the above method, no blue color is seen to deposit on the surface of the dip stick. When control fecal material having E. histolytica antigen added is tested, blue color is seen to deposit on the surface of the dip stick, indicating the presence of bound E. histolytica antigen.

EXAMPLE 2

The device and method for detecting E. histolytica antigen in human fecal material, as described in Example 1, may be modified by employing an alternative substrate for color development of bound HRP-monoclonal anti-E. histolytica antibody conjugate, viz. a solution of 0.2 mg per ml of ABTS (azino-6-benzthiazoline-6 sulfonate) and 1.5 mM hydrogen peroxide in PBS may be substituted for the 4-chloronaphthol substrate. When a dip stick having bound analyte labeled with the HRP enzyme conjugate is contacted with this ABTS/-peroxide substrate solution, a blue-green color develops in the substrate liquid. When control fecal material without E. histolytica antigen is tested by this method, no blue-green color is seen to develop in the substrate solution within a 15 minute reaction time. When control feed material with 1000 trophs of added E. histolytica antigen is processed by this method, a blue-green color is seen to form in the substrate solution.

EXAMPLE 3

The immunoassay incubation device and method for detecting E. histolytica antigen in human fecal samples, as described in Examples 1 and 2, may be modified by substituting a coated polystyrene sphere for the coated dip stick (15). Coated polystyrene spheres may be prepared by soaking polystyrene spheres, e.g. 5/16" in diameter (Precision Plastic Ball Co.; Chicago, Ill.) in a solution of 1-2 micrograms/ml of anti-E. histolytica monoclonal antibody, in sodium borate buffer, pH 9.2. After soaking four hours, anti-E. histolytica monoclonal antibody has passively absorbed onto the surface of the polystyrene spheres. The coated spheres are then removed from the antibody solution and soaked in a second solution of 1% bovine serum albumin (BSA) in PBS for three hours. Coating the spheres with BSA reduces nonspecific binding to the coated spheres. The spheres are then washed in distilled water and dried at ambient temperature overnight. The uniformity of the coating is improved if the spheres are moved continuously by slow rotation during both soaking steps. A conventional laboratory bench rocker may be employed for rotating the spheres during the soaking steps. It is convenient to carry out the soaking steps in T75 tissue culture-type flasks (Falcon Plastics or equivalent).

If a coated sphere is substituted for a coated dip stick (15), the immunoassay procedure described in examples 1 and 2 may also be modified. After the fecal sample is homogenated, the coated sphere may be introduced into the incubation chamber (5) and incubated with the extracted components of the homogenate for approximately 20 minutes in order to provide an opportunity for E. histolytica antigen to bind to the coated sphere. After this first incubation step, the sphere is then removed from the incubation chamber (5), preferably with forceps, and placed into a clean test tube. The sphere is then washed three times with cold distilled water to remove unbound components. The washed coated sphere is then incubated for 20 minutes in a solution of anti-E. histolytica-HRP enzyme conjugate (0.5 ml), as provided in Examples 1 and 2, in order to label the bound E. histolytica antigen. After this second incubation, the sphere is washed once again with cold distilled water to remove unbound enzyme conjugate. The HRP labeled spheres are then color developed, as described in Examples 1 or 2, using the 4-chloronaphthol or ABTS substrates, to detect the presence of E. histolytica antigen in the fecal sample.

EXAMPLE 4

An immunoassay incubation device may be specially constructed for detecting sample material which contains Chlamydia trachomatis and which is collected and carried on a sample collection swab. Such an immunoassay incubation device includes a mechanism for extracting microbial sample material from sample collection swabs and includes a dip stick (15) sensitized for detecting Chlamydia trachomatis antigen.

An immunoassay incubation device which is constructed for extracting sample material from swabs should include access for such swabs between the insert (4) and the vessel (1). The device should include a clearance of approximately 4 mm between the outer wall of the insert (4) and the inner wall of the vessel (1), i.e. sufficient clearance for the swab to fit snugly. An insert (4) introduced into the vessel (1) should be axially centered within the vessel (1) and rotatable. The screen (6)

for this insert (4) may include approximately twenty holes in the lower half of the insert for allowing liquid to freely pass between the incubation chamber (5) and the lower portion of the vessel (2). The lower half of the insert (4) and/or the vessel (1) should also include one or more columnar protrusions rising from the wall of the the insert (4) and/or the vessel (1). When a swab is introduced into the device and the insert (4) is rotated with respect to the vessel (1), the swab also rotates and rolls across the columnar protrusions, causing sample material to be squeezed from the swab.

To operate the device, a swab ladened with sample material is first placed into the vessel (1). Sample material may consist of chlamydial elementary bodies obtained from a culture of McCoy cells infected with Chlamydia trachomatis L2 (ATCC Cat. VR902B) grown in DMEM medium at 37 degrees centigrade with 10% CO(2), passaged in 24 hour intervals. The cotton portion of the swab, ladened with sampled material, should be positioned in the bottom half of the vessel (1) with its axis parallel to the axis of the vessel (1). The insert (4) is then introduced into the vessel (1) and axially fixed. The swab then lies between the insert (4) and the vessel (1). A volume of PBS is then added to the vessel (1), so as to submerse the swab. This liquid flows freely between the incubation chamber (5) and the vessel (1). The insert (4) is then rotated approximately 180 degrees back and forth about twenty times. This motion results in an alternate squeezing and release of the swab as it rotates between the columnar protrusions and the opposing wall of the insert (4) and/or vessel (1). In this way, the liquid in the swab containing the infectious organisms is efficiently extracted from the swab and suspended into the extracting medium. When this extraction is completed, the swab is removed and a polystyrene dip stick (15) is introduced into the incubation chamber (5) in order to assay analyte extracted from the swab.

The dip stick (15) can be constructed using the same method as described in Example 1, except that monoclonal anti-chlamydial antibodies are substituted for monoclonal anti-E. histolytica antibodies. Monoclonal anti-chlamydial antibodies are prepared by injection of Chlamydia trachomatis, L2 strain (ATCC, Cat. No. VR902B) into Balb/c mice (Jackson laboratories). Fusion of the resulting immune spleen cells and production of monoclonal antibodies is conducted according to the procedure described by Kohler & Milstein. The resultant monoclonal anti-chlamydial antibodies are then employed to construct dip sticks (15), as described in Example 1.

The immunoassay incubation devices can be prepackaged with antibody enzyme conjugate for labeling bound chlamydia antigen, e.g., HRP-anti-chlamydia monoclonal antibody conjugate. In a device prepackaged with enzyme conjugate, the screen (6) does not extend below a 3 mm margin above the bottom of the incubation chamber (5), such that a well (20) is present which allows a small amount of reagent to be deposited and maintained. The HRP-anti-chlamydia monoclonal antibody conjugate, prepared according to the method of Nakane (supra), is dissolved 0.5 mg per ml in 1% sucrose solutions containing 0.05% Tween-20. One hundred microliters of this solution is then dispensed into the well (20) of each incubation chamber (5) and allowed to dry overnight.

When PBS is added to the vessel (1) for extracting sample material from the swab, the antibody-enzyme conjugate, previously deposited and dried in the well (20) of the incubation chamber (5), redissolves and reacts with extracted chlamydial antigen. Extracted chlamydial antigen which also binds to the solid phase immunological reagent, i.e. the monoclonal anti-chlamydia antibody coated onto the polystyrene dip stick (15), will be either prelabeled or subsequently labeled with the HRP-anti-chlamydia antibody conjugate. Bound chlamydial antigen will form a sandwich consisting of polystyrene immobilized antibody-chlamydial antigen-monoclonal enzyme conjugate.

After extracting sample material from the swab and incubating the extract with the dip stick (15) for a period of two hours, the dip stick (15) is then removed and washed under a stream of distilled water. The HRP label which remains bound to the dip stick (15) is then color developed to detect the presence of chlamydial antigen. The dip stick (15) may be color developed using either the ABTS/peroxide substrate, described in Example 2, or the 4-chloronaphthol/peroxidase solution described in Example 1. When a swab which had been contacted with tissue culture medium of McCoy cells infected with Chlamydia trachomatis is extracted and tested using the ABTS assay procedure, a blue-green color is found to be generated in the substrate solution after approximately ½ hour; the substrate solutions obtained from swabs without chlamydial antigen remain clear. When a swab with chlamydial antigen is extracted and tested using the 4-chloronaphthol assay procedure, a blue color is seen to adhere to the surface of the dip stick; no blue color is seen to form on the surface of the dip stick when swabs without chlamydial antigen are tested.

EXAMPLE 5

Detection of Herpes II Antigen

An immunoassay incubation device may be specifically constructed for detecting sample material which contains herpes simplex virus and which is collected and carried on a sample collection swab. The structure of the device may be identical to the structure described in Example 4. However, the chemistry of the devices differ because the dip stick (15) of the present device is immunologically sensitized to detect herpes simplex virus antigen (HSV) and the well (20) of the incubation chamber (5) includes a dried deposit of soluble enzyme antibody conjugate having a specificity for labeling herpes simplex virus antigen.

The dips stick (15) may be constructed using the same method as described in Example 1, except that polyclonal antibodies to herpes simplex virus are substituted for monoclonal anti-I. histolytica antibodies.

The antibody enzyme conjugate may be constructed from a conjugation between anti-HSV II monoclonal antibody (obtained from cell line 105S, National Cancer Institute, Bethesda, Maryland) and glucose oxidase. The glucose oxidase is coupled to anti-HSV II monoclonal antibody according to the procedure of Nakane (supra). The antibody enzyme conjugate is dissolved 0.5 mg per ml in 1% glucose solutions containing 0.05% Tween-20. 100 microliter aliquots of the solution are dispensed into the well (20) of each incubation chamber (5) and allowed to dry overnight.

The assay procedure begins by absorbing sample material with a sterile swab. Sample material may be obtained from the media of a culture of VERO cells (ATCC Catalog Number CCL81) grown in DMEM medium at 37 degrees centigrade, 10% CO(2), and infected with herpes simplex virus II (ATCC Catalog Number VR734). Media taken from uninfected VERO cells grown under identical conditions may serve as a negative control. The immunoassay incubation devices are then employed to extract sample material from the sample collection swabs using an aliquot of PBS, as described in Example 4. The swab may then be kept in place while a dip stick (15) is inserted into the incubation chamber (5) and allowed to incubate with the extracted swab solution for approximately 4 hours. During the extraction process and subsequent incubation period, the deposit of dried antibody enzyme conjugate in the well (20) of the incubation chamber (5) redissolves and reacts with herpes antigen extracted from the swab. The glucose oxidase labeled herpes antigen forms a sandwich with the coated dip stick (15), consisting of the dip stick immobilized anti-HSV antibody, HSV antigen, and monoclonal anti-HSV II glucose oxidase conjugate.

After the incubation period, the dip stick (15) is color developed to detect bound glucose oxidase and to detect sample materials with HSV antigen. The dip stick (15) is removed from the incubation chamber (5) and washed under a stream of distilled water to remove unbound antibody enzyme conjugate. The dip stick (15) is then incubated in 1 ml of substrate solution, e.g. 110 mM glucose, 0.007 mg per ml horseradish peroxidase (Sigma), and 0.2 mg per ml ABTS in PBS. After one hour of incubation, if the sample material contains HSV antigen, a blue-green color will be seen to develop in this ABTS substrate solution. If the sample material contains no HSV antigen or low levels of HSV antigen, no color will be seen to develop in this ABTS substrate solution.

EXAMPLE 6

Detection of Human Hemoglobin

Figure 9:
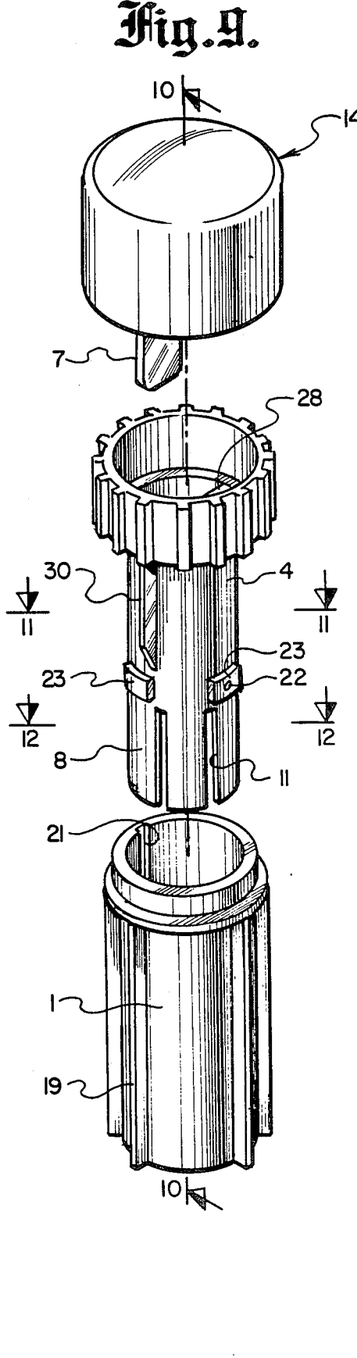
FIG. 9 is an exploded view in perspective of another alternative embodiment of the immunoassay incubation device illustrating a valve for controlling the flow of homogenized sample from the extractor into the incubation chamber.
Figure 10:
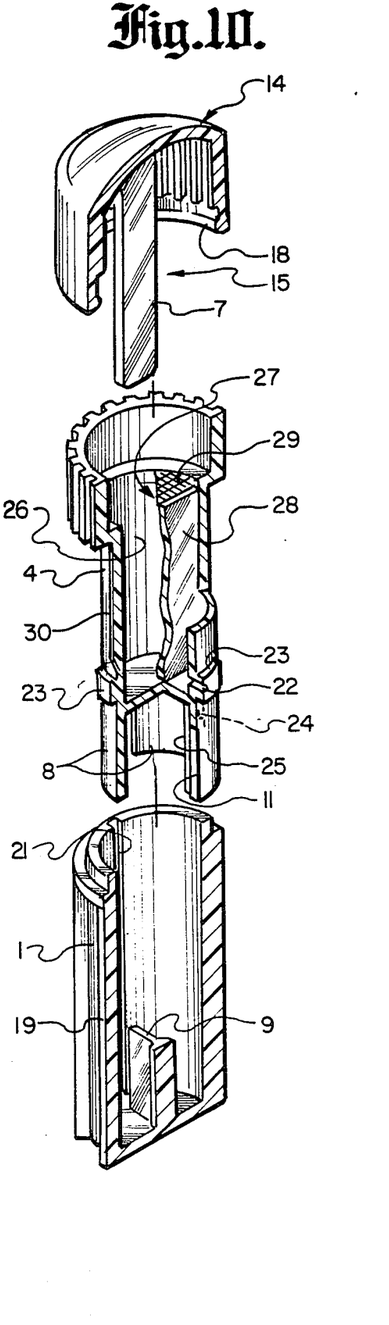
FIG. 10 is a sectional view of the immunoassay incubation device of FIG. 9.
Figure 11:
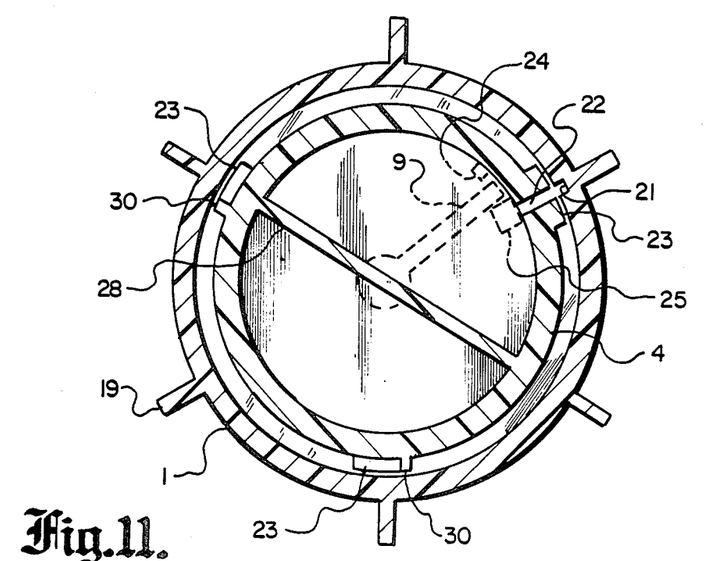
FIG. 11 is a sectional view of the immunoassay incubation device of FIG. 9.
Figure 12:
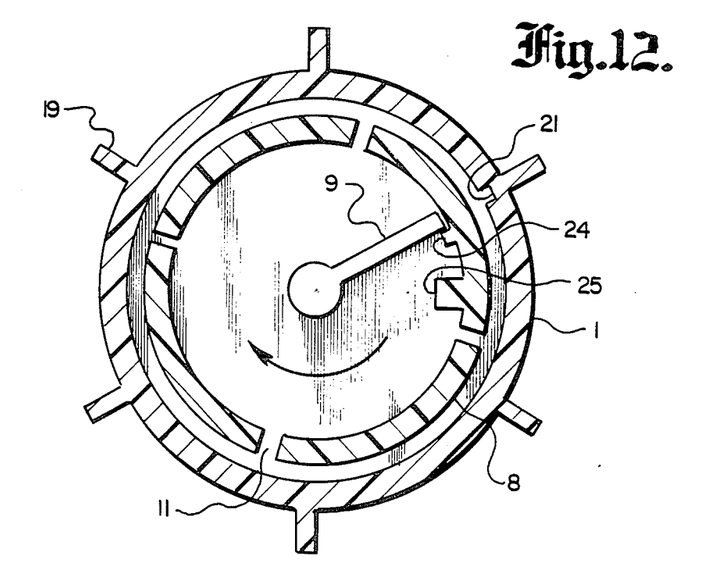
FIG. 12 is a sectional view of the immunoassay incubation device of FIG. 9.

An immunoassay incubation device for detecting the presence of hemoglobin from human stool samples may be constructed generally as illustrated in FIGS. 9 and 10. The device includes three separate pieces: a homogenizer or vessel (1), an insert (4), and a cap (14) and dip stick (15). The homogenizer is a round vessel of approximately 4 milliliters capacity which has one or more stationary vanes (9) on its floor to facilitate homogenization. The insert (4) is designed as one piece with two separate functions. The scoop of sampler (8) is constructed as a dead-end tube located at the base of the insert (4), which carries 4 to 8 narrow vertical slots (11) running its length. The incubation chamber portion of the insert is made up of two or three separate incubation chambers or wells (26 & 27), one of which carries a small hole (22) in its wall. The small hole (22) extends radially through a protuberance (23) in the wall of the insert and is occluded by contact with the wall of the vessel (1). The vessel (1) includes a depression (21). When the insert (4) is properly aligned with the vessel (1), the hole (22) will align with the depression (21) and sample fluid will pass from the vessel (1) into the first incubation chamber (26). The other incubation chamber or chambers (27) are sealed with Mylar foil (29), which is to be punctured during use as described below. These sealed incubation chambers (27) do not have a hole (22) and cannot communicate with the vessel (1). The cap (14) and dip stick (15) fit onto the top of the vessel (1) in a water-tight manner; the dip stick (15) is attached to the cap (14) and extends down into the incubation chamber (23) to within a few millimeters of the incubation chamber floor. The dip stick (15) is located eccentrically with respect to the cap (14) so that it may be positioned in one or the other of the incubation chambers (27 & 27) by proper rotation of the cap (14).

In use, a stool sample is placed in the vessel (1) by means of the scoop or sampler (8); 2 mls of phosphate buffered saline, as described above, is added, and the stool sample is then homogenized by rotation of the cap (14) from side to side. Horseradish peroxidase (HRP) covalently coupled to anti-human hemoglobin antibody is added to the homogenization fluid. This conjugate is prepared by the method of Nakane et al. as described above from anti-human hemoglobin antibody (Calbiochem-Behring Corp., La Jolla, Calif., U.S.A. or Australian Monoclonal Development Co.). Once homogenization is complete, the cap (14) is turned back to its normal position and the hole (22) in the incubation chamber (26) is thereby closed, preventing the leakage of reagents out of the incubation chamber (26).

Once the homogenized sample fluid enters the first incubation chamber (26), the assay member (7) becomes exposed to sample antigens, including human hemoglobin. The surface of the assay member (7) has previously been coated with monoclonal mouse anti-human antibody (Australian Monoclonal Development Co.), as described in earlier Examples. Consequently, when exposed to the homogenized fluid sample, the assay member (7) will then bind to any human hemoglobin which is present therein. During the incubation process, the anti-human hemoglobin conjugate of HRP will also bind to the human hemoglobin, and, in turn, will become linked, via the human hemoglobin, to the assay member. The incubation of the assay member (7) with the sample fluid is then allowed to proceed for approximately 15 minutes.

The assay member (7) is then washed and inserted into the second incubation chamber (27) for color development. In order to enter the second incubation chamber (27), the Mylar foil (29) covering the chamber (27) must be punctured, preferably with the dip stick (15). Either the chloronapthol substrate, as described in Example 1, or the azino-6-benzthiazoline-6 sulfonate substrate, as described in Example 2, may be used as substrate for the anti-human hemoglobin conjugate of HRP, which remains bound to the assay member (7) in proportion to the presence of human hemoglobin in the sample fluid.

Alternatively, if a device with three incubation chambers (23) is used, the conjugate or detect antibody is not added to the homogenization fluid but is present in the second incubation chamber (27), and the substrate for color development is present in the third incubation chamber (27).

What is claimed is:

1. An immunoassay incubation device for extracting a soluble analyte from a solid or semisolid sample into a liquid medium, for separating the soluble analyte from unextracted components of the solid or semisolid sample, and for assaying the soluble analyte, the device comprising:
   a vessel for receiving and containing the solid or semisolid sample and the liquid medium,
   a means for extracting the soluble analyte from the solid or semisolid sample into the liquid medium, said extraction means removably contained within said vessel, an incubation chamber removably contained within said vessel, said incubation chamber defining one or more apertures positively immersible within the liquid medium of said vessel, the apertures having a cross sectional area sufficiently large for passing detectable quantities of the soluble analyte and a cross sectional diameter sufficiently small for blocking passage of unextracted components between said vessel and said incubation chamber, and a solid phase assay member coated with a binding immunological reagent inserted within said incubation chamber when assaying the soluble analyte therein, the apertures of said incubation chamber effectively screening said solid phase assay member from contact with unextracted components from said vessel when said solid phase assay member is inserted into said incubation chamber.

2. An immunoassay incubation device as described in claim 1 wherein the solid or semisolid sample is fecal material and wherein:

the apertures have a cross sectional diameter of approximately one millimeter.

3. An immunoassay incubation device as described in claim 2 wherein:

the binding immunological reagent is an anti-E. histolytica antibody.

4. An immunoassay incubation device as described in claim 2 wherein:

the binding immunological reagent is an anti-chlamydia antibody.

5. The immunoassay incubation device as described in claim 2 wherein:

the binding immunological reagent is an anti-HSV antibody.

6. An immunoassay incubation device as described in claim 2 wherein:

the binding immunological reagent is an anti-human hemoglobin antibody.

7. An immunoassay incubation device for extracting a soluble analyte from a solid or semisolid sample into a liquid medium, for separating the soluble analyte from unextracted components of the solid or semisolid sample, and for assaying the soluble analyte, the device comprising:

a vessel for receiving and containing the solid or semisolid sample and the liquid medium, a means for extracting the soluble analyte from the solid or semisolid sample into the liquid medium, said extraction means removably contained within said vessel, an incubation chamber removably contained within said vessel, said incubation chamber defining one or more apertures positively immersible within the liquid medium of said vessel, the apertures having a cross sectional area sufficiently large for passing detectable quantities of the soluble analyte and a cross sectional diameter sufficiently small for blocking passage of unextracted components between said vessel and said incubation chamber, a solid phase assay member coated with a binding immunological reagent inserted within said incubation chamber when assaying the soluble analyte therein, the apertures of said incubation chamber effectively screening said solid phase assay member from contact with unextracted components from said vessel when said solid phase assay member is inserted into said incubation chamber, and a cap for sealing off said vessel, said cap connected to and serving as a handle for said solid phase assay member for positioning said solid phase assay member within said incubation chamber, said cap engageable to said extraction means while sealing off said vessel for actuating said extraction means by means of rotational motion for extracting the soluble analyte from the solid or semisolid sample within said vessel.

8. An immunoassay incubation device as described in claim 7 wherein:

said extraction means includes one or more fixed vanes attached to said vessel and one or more rotatable vanes attached to said incubation chamber for extracting the sample into the liquid medium.

9. An immunoassay incubation device as described in claim 7 wherein:

said extraction means includes one or more fixed grinding members attached to said vessel and one or more rotatable grinding members attached to said incubation chamber for extracting the sample into the liquid medium.

10. An immunoassay incubation device as described in claim 7 wherein:

said extraction means includes one or more fixed serrated surfaces attached to said vessel and one or more rotatable serrated surfaces attached to said incubation chamber for extracting the sample into the liquid medium.

11. An immunoassay incubation device as described in claim 7 further comprising:

a scoop for securing a plug of the solid or semisolid sample, said scoop joined to said incubation chamber for introducing the plug of solid or semisolid sample to said vessel.

12. An immunoassay incubation device as described in claim 11 wherein:

said scoop is engagable with said extraction means for supplying the plug of solid or semisolid sample to said extraction means and for axially centering said incubation chamber within said vessel.

13. An immunoassay incubation device as described in claim 7 further comprising:

a means for defining a well within the incubation chamber below the apertures for retaining a deposit of dried labelled immunological reagents.

14. An immunoassay incubation device as described in claim 7 wherein:

said solid phase assay member is incorporated onto a dip stick, the dip stick being attached to said cap and being inserted within the incubation chamber with said cap attached to said vessel when assaying the soluble analyte.

15. An immunoassay incubation device as described in claim 7 for assaying two or more sample soluble analytes wherein:

said solid phase assay member including two or more separate subsections, each subsection differing from the remaining subsections with respect to its specificity for assaying the sample soluble analytes.

16. An immunoassay incubation device for extracting a soluble analyte from a solid or semisolid sample into a liquid medium, for separating the soluble analyte from unextracted components of the solid or semisolid sample, and for assaying the soluble analyte, the device comprising:

a vessel for receiving and containing the solid or semisolid sample and the liquid medium, a means for extracting the soluble analyte from the solid or semisolid sample into the liquid medium, said extraction means removably contained within said vessel, an incubation chamber removably contained within said vessel, said incubation chamber defining one or more apertures positively immersible within the liquid medium of said vessel, the apertures having a cross sectional area sufficiently large for passing detectable quantities of the soluble analyte and a cross sectional diameter sufficiently small or blocking passage of unextracted components between said vessel and said incubation chamber, a solid phase assay member coated with a binding immunological reagent inserted within said incubation chamber when assaying the soluble analyte therein, the apertures of said incubation chamber effectively screening said solid phase assay member from contact with unextracted components from said vessel when said solid phase assay member is inserted into said incubation chamber, a cap for sealing off said vessel, said cap connected to and serving as a handle for said solid phase assay member for positioning said solid phase assay member within said incubation chamber, said cap engagable to said extraction means while sealing off said vessel for actuating said extraction means by means of rotational motion for extracting the soluble analyte from the solid or semisolid sample within said vessel, said solid phase assay member incorporated onto an elongated dip stick, the elongated dip stick attached to said cap and insertable into the incubation chamber while said cap seals off said vessel, and a means for defining a well within the incubation chamber below the apertures for retaining a deposit of dried labelled immunological reagents.

17. An immunoassay incubation device for extracting a soluble analyte from a solid or semisolid sample into a liquid medium, for separating the soluble analyte from unextracted components of the solid or semisolid sample, and for assaying a soluble analyte, the device comprising:

a vessel for receiving and containing the solid or semisolid sample and the liquid medium, a means for extracting the soluble analyte from the solid or semisolid sample into the liquid medium, said extraction means removably contained within said vessel, an incubation chamber removably contained within said vessel, a valve incorporated into said incubation chamber immersible with said incubation chamber within the liquid medium for controlling the passage of the liquid medium and the soluble analyte and for blocking the passage of unextracted components between said vessel and said incubation chamber, and a solid phase assay member coated with a binding immunological reagent inserted within said incubation chamber when assaying the soluble analyte therein, said valve effectively screening said solid phase assay member from contact with unextracted components from said vessel when said solid phase assay member is inserted into said incubation chamber.

18. An immunoassay incubation device as described in claim 17 wherein:

said valve including a radial protuberance protruding outward from said incubation chamber, the radial protuberance defining a valve hole communicating between said incubation chamber and said vessel, the valve hole occludable by contact with said vessel, said vessel including a depression which, when aligned with the valve hole, opens the valve hole for allowing the passage of liquid medium and soluble analyte from said vessel to said incubation chamber while blocking the passage of unextracted components.

19. An immunoassay incubation device as described in claim 17 further comprising:

a cap for sealing off said vessel, said cap connected to and serving as a handle for said solid phase assay member for positioning said assay member within said incubation chamber, said cap engagable to said extraction means while sealing off said vessel for actuating said extraction means by means of rotational motion for extracting the soluble analyte from the solid or semisolid sample within said vessel, said cap engagable to said valve for opening and closing said valve by means of rotational motion.

20. An immunoassay incubation device for extracting a soluble analyte from a solid or semisolid sample into a liquid medium, for separating the soluble analyte from unextracted components of the solid or semisolid sample, and for assaying a soluble analyte, the device comprising:

a vessel for receiving and containing the solid or semisolid sample and the liquid medium, a means for extracting the soluble analyte from the solid or semisolid sample into the liquid medium, said extraction means removably contained within said vessel, an incubation chamber removably contained within said vessel, a valve incorporated into said incubation chamber immersible with said incubation chamber within the liquid medium for controlling the passage of the liquid medium and the soluble analyte and for blocking the passage of unextracted components between said vessel and said incubation chamber, a solid phase assay member coated with a binding immunological reagent inserted within said incubation chamber when assaying the soluble analyte therein, a cap for sealing off said vessel, said cap connected to and serving as a handle for said solid phase assay member for positioning said assay member within said incubation chamber, said cap engagable to said extraction means while sealing off said vessel for actuating said extraction means by means of rotational motion for extracting the soluble analyte from the solid or semisolid sample within said vessel, said cap engagable to said valve for opening and closing said valve by means of rotational motion, a first stop for limiting the rotational motion of the cap for maintaining said valve in a closed position while actuating said extraction means, and a second stop beyond said first stop for maintaining said valve in an open position.

21. An immunological incubation device for extracting a soluble analyte from a solid or semisolid sample into a liquid medium, for separating the soluble analyte from unextracted components of the solid or semisolid sample, and for assaying a soluble analyte, the device comprising:

a vessel for receiving and containing the solid or semisolid sample and the liquid medium, a means for extracting the soluble analyte from the solid or semisolid sample into the liquid medium, said extraction means containable within said vessel, a first incubation chamber removably contained within said vessel, a second incubation chamber removably contained within said vessel, labelled immunological reagents contained within said second incubation chamber, a means for sealing off said labelled immunological reagents within second chamber for preventing the entry of the liquid medium into said second chamber, a valve incorporated into said first incubation chamber immersible with said incubation chamber within the liquid medium for controlling the passage of the liquid medium and the soluble analyte and for blocking the passage of unextracted components between said vessel and said first incubation chamber, and a solid phase assay member coated with a binding immunological reagent inserted within said first incubation chamber when assaying the soluble analyte therein, said valve effectively screening said solid phase assay member from contact with unextracted components from said vessel when said solid phase assay member is inserted into said first incubation chamber, said solid phase assay member capable of breaking said sealing means and being inserted into said second incubation chamber for contacting said labelled immunological reagents for developing said solid phase assay member and detecting the soluble analyte attached thereto.

22. A method for detecting a soluble analyte sequestered within a solid or semisolid sample, the method comprising the following steps:

Step (a): loading an immunoassay incubation device with a liquid medium,

Step (b): introducing the solid or semisolid sample into the immunoassay incubation device, then Step (c): extracting the soluble analyted from the solid or semisolid sample into the liquid medium within the immunoassay incubation device, then Step (d): allowing the liquid medium and soluble analyte to pass into an incubation chamber housed within the immunoassay incubation device while blocking the passage of unextracted components into the incubation chamber, then Step (e): contacting a solid phase assay member with the soluble analyte, the solid phase assay member inserted within the incubation chamber and partially submersed in liquid medium therein, the solid phase assay member coated with a binding immunological reagent for binding the soluble analyte, then Step (f): removing the solid phase assay member from the incubation chamber, and then Step (g): measuring the soluble analyte bound to the solid phase assay member.

23. A method for detecting a soluble analyte as described in claim 22 wherein:

in Step (c) the extraction of the soluble analyte from the solid or semisolid sample is actuated by rotating a cap which also seals off the immunoassay incubation device.

24. A method for detecting a soluble analyte as described in claim 22 wherein:

in Step (d) the passage of liquid medium and soluble analyte into the incubation chamber is controlled by means of a valve.

25. A method for detecting a soluble analyte as described in claim 22 wherein:

in Step (g) the measurement of the soluble analyte bound to the solid phase assay member is accomplished by inserting the solid phase assay member into a second incubation chamber housed within the immunoassay incubation device, the second incubation chamber including a labelled immunological reagent and a means for sealing the labelled immunological reagent within the second chamber.

* * * * *